(12) United States Patent
Williams

(10) Patent No.: US 10,080,678 B2
(45) Date of Patent: Sep. 25, 2018

(54) AMBIDEXTROUS, COMBINATION WRIST AND THUMB BRACE

(71) Applicant: Mike Williams, Logan, UT (US)

(72) Inventor: Mike Williams, Logan, UT (US)

(*) Notice: Subject to any disclaimer, the term of this patent is extended or adjusted under 35 U.S.C. 154(b) by 180 days.

(21) Appl. No.: 14/941,483

(22) Filed: Nov. 13, 2015

(65) Prior Publication Data
US 2017/0135840 A1  May 18, 2017

(51) Int. Cl.
*A61F 5/00* (2006.01)
*A61F 5/01* (2006.01)
*A61F 5/058* (2006.01)

(52) U.S. Cl.
CPC ........ *A61F 5/0118* (2013.01); *A61F 5/05825* (2013.01); *A61F 5/05866* (2013.01)

(58) Field of Classification Search
CPC ........ A61F 5/0118; A61F 5/0104; A61F 5/01; A61F 5/05866; A61F 5/05825; A61F 5/058; A61F 5/05858; A61F 5/05875
See application file for complete search history.

(56) References Cited

U.S. PATENT DOCUMENTS

| | | | | |
|---|---|---|---|---|
| 5,759,166 A * | 6/1998 | Nelson | ............... | A61F 5/0118 602/21 |
| 6,398,748 B1 * | 6/2002 | Wilson | ............... | A61F 5/0118 128/869 |
| 6,893,410 B1 * | 5/2005 | Hely | ............... | A61F 5/0118 602/21 |
| 7,056,298 B1 * | 6/2006 | Weber | ............... | A61F 5/0118 2/16 |
| 7,824,352 B2 * | 11/2010 | Jaccard | ............... | A61F 5/05866 602/20 |
| 8,114,041 B2 | 2/2012 | Wyatt et al. | | |
| 8,235,927 B2 * | 8/2012 | Bauerfeind | ............... | A61F 5/0118 602/20 |

\* cited by examiner

*Primary Examiner* — Victoria J Hicks
(74) *Attorney, Agent, or Firm* — Preston P. Frischknecht; Project CIP

(57) ABSTRACT

The disclosure concerns a wrist and thumb brace with a wrist brace portion for stabilizing a user's wrist, the wrist brace portion having a first aperture adapted for a user's right thumb when the brace is on a user's right hand, and a second aperture adapted for a user's left thumb when the brace is on a user's left hand, the first and second apertures facilitating ambidextrous use of the brace; and a thumb brace portion for stabilizing a user's thumb, the thumb brace portion removably attachable to the wrist brace portion at a first location adjacent to the first aperture when the brace is on a user's right hand, the thumb brace portion removably attachable to the wrist brace portion at a second location adjacent to the second aperture when the brace is on a user's left hand.

8 Claims, 4 Drawing Sheets

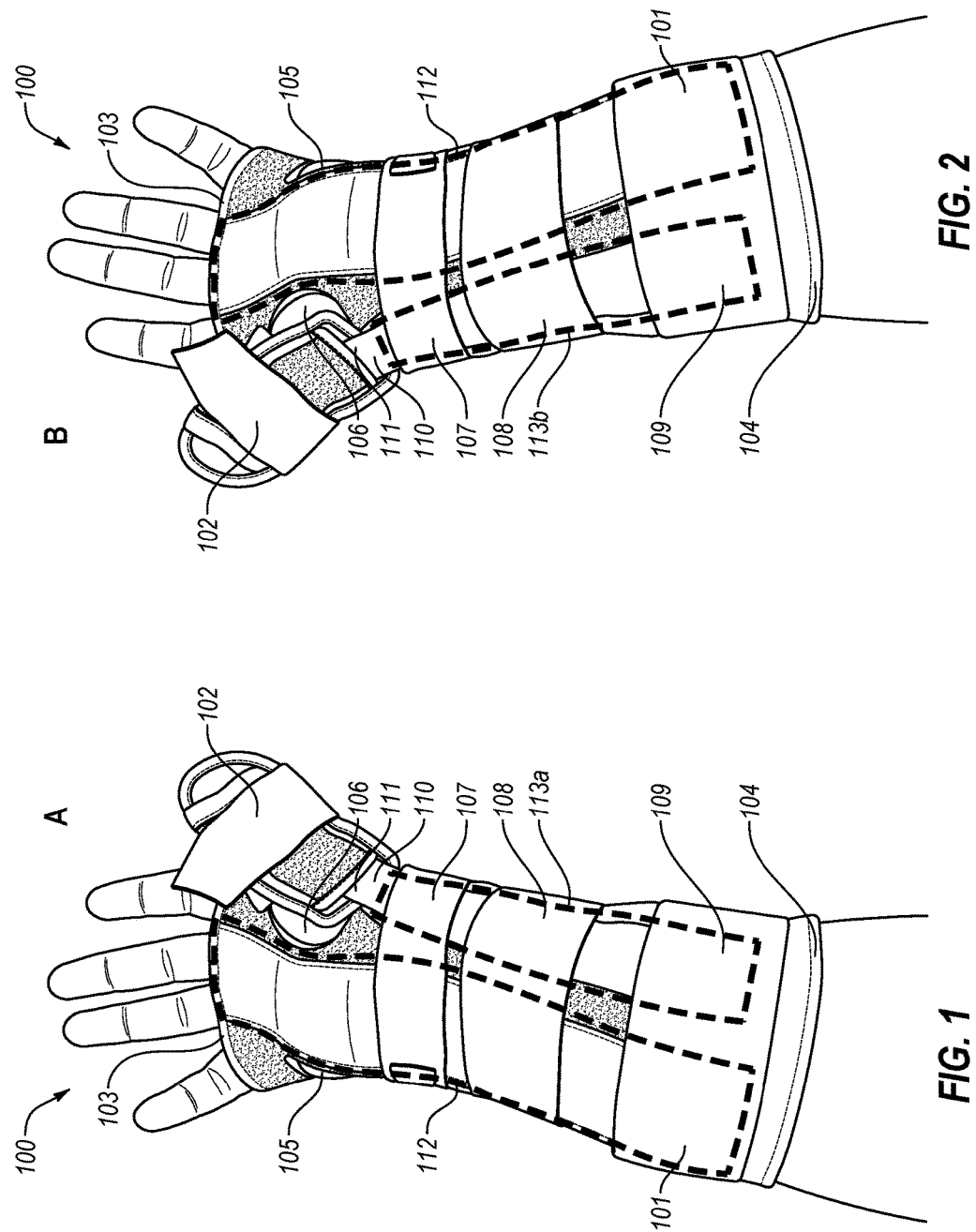

US 10,080,678 B2

AMBIDEXTROUS, COMBINATION WRIST AND THUMB BRACE

PRIORITY CLAIM

This patent application claims priority to U.S. Provisional Application 62/079,667, filed on Nov. 14, 2014.

BACKGROUND OF THE INVENTION

Various injuries, post-operative conditions, and other scenarios call for stabilization of the wrist and/or thumb. Wrist braces, thumb braces, and even combination wrist and thumb brace are known in the prior art. However, there is a dearth of robust and versatile combination braces that provide for both right and left handed use and use as a stand-alone wrist brace. This problem leads to inventory control issues when multiple and varying configurations of braces must be held to treat a variety of different presentations.

What is needed is a robust and versatile combination brace that is designed for both right and left handed use, and which can be selectively used as a combination wrist and thumb brace, or as a stand-alone wrist brace.

SUMMARY OF THE INVENTION

In accordance with the above, a new and innovative, ambidextrous, combination wrist and thumb brace is provided. The problems of achieving a single brace unit designed for both right and left handed use, and which can be selectively used as a wrist and thumb brace, or as a stand-alone wrist brace, is solved. Embodiments of the present invention include, a combination wrist and thumb brace having a wrist brace portion with a first aperture for a user's right thumb and a second aperture for a user's left thumb, the first and second apertures configured to allow ambidextrous use of the brace; the brace further having a thumb portion removeably attachable to the wrist brace portion at a first location adjacent to the first aperture, or alternatively, at a second location adjacent to the second aperture.

These and other aspects of the present invention will become more fully apparent from the following description and appended claims, or may be learned by the practice of the invention as set forth hereinafter.

BRIEF DESCRIPTION OF THE FIGURES

To further clarify the above and other aspects of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The drawings may not be drawn to scale. The invention will be described and explained with additional specificity and detail through the use of the accompanying drawings in which:

FIG. 1 is a perspective view of a combination wrist and thumb brace in a right handed configuration.

FIG. 2 is a perspective view of a combination wrist and thumb brace in a left handed configuration.

DETAILED DESCRIPTION OF THE ILLUSTRATED EMBODIMENT

The present invention in its various embodiments, some of which are depicted in the figures herein, is an ambidextrous, combination wrist and thumb brace. FIG. 1 depicts one embodiment of an ambidextrous, combination wrist and thumb brace 100. In the illustrated embodiment, the brace 100 is shown in a right handed configuration A. The brace is comprised of a wrist brace portion 101 and a thumb brace portion 110.

Figure 3:
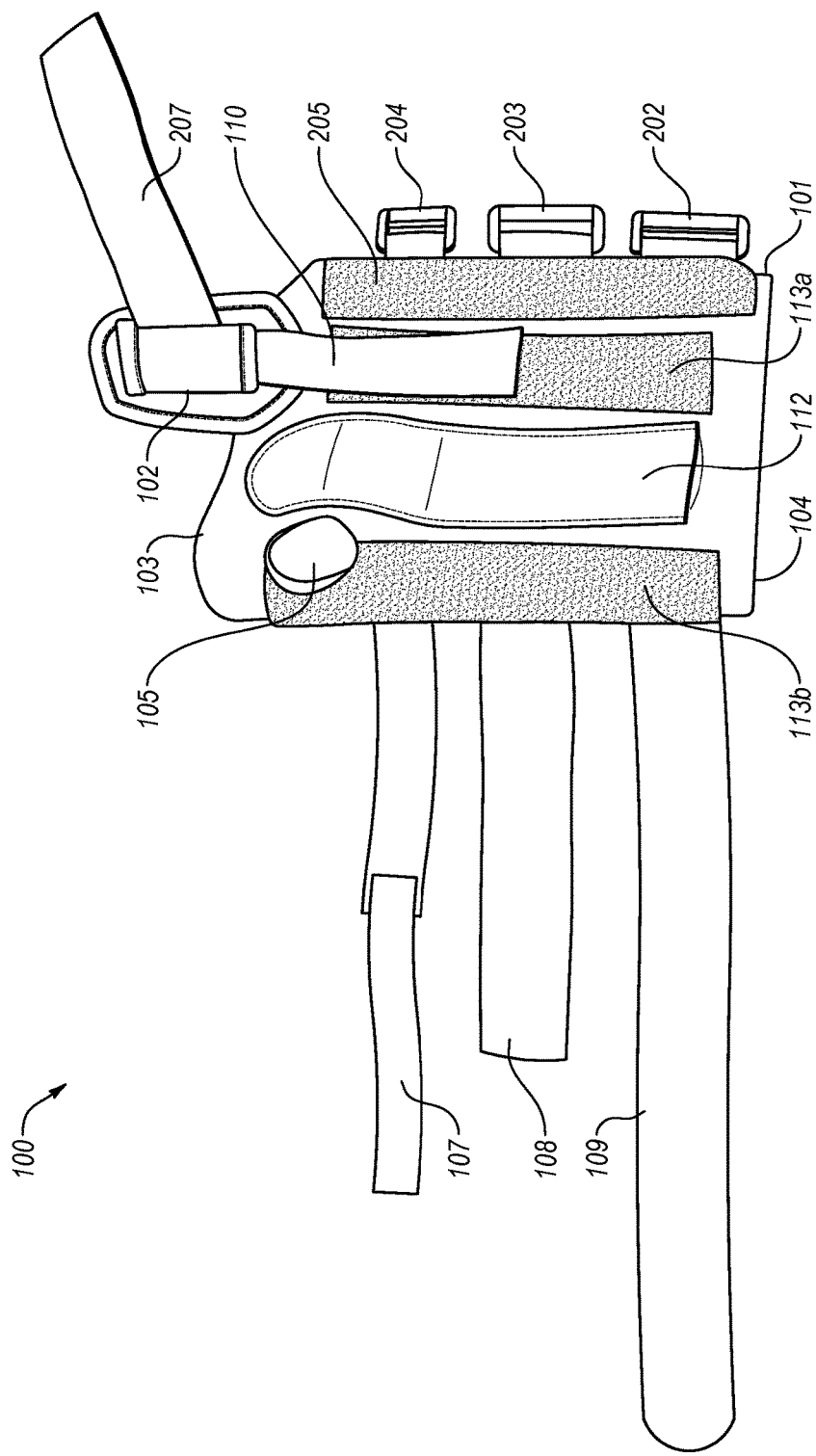
FIG. 3 is a front view of a combination wrist and thumb brace.

Referring to FIGS. 1 and 3, in preferred embodiments the wrist brace portion 101 is generally constructed of neoprene with various softer interior material linings (not shown). However, any number of materials may be used without departing from the purpose and scope of the invention. The wrist brace portion 101 generally forms a tube or tunnel when in use, with a proximal opening 104 and a distal opening 103. Adjacent to the distal opening 103, the wrist brace portion 101 also has a first thumb opening 106 that facilitates positioning of a users' right hand thumb when the brace is used to stabilize a user's right hand, and a second thumb opening 105 that facilitates positioning of a users' left hand thumb when the brace is used to stabilize a user's left hand.

The wrist brace portion 101 may also have one or more support straps 107, 108, 109 which may be wrapped perpendicular to and around the wrist brace portion tube (see FIGS. 1 & 2) in order to cinch, secure, and/or support the wrist brace portion 101 onto a user's arm and/or wrist. These straps may be constructed of hook and loop material such as Velcro, or any number of other materials. Cinch loops 202, 203, 204 or other alternative fasteners may be incorporated. In the particular illustrated embodiments shown, the wrist brace portion 101 has first 107, second 108, and third 109 support straps, distributed along the wrist brace portion 101.

Figure 6:
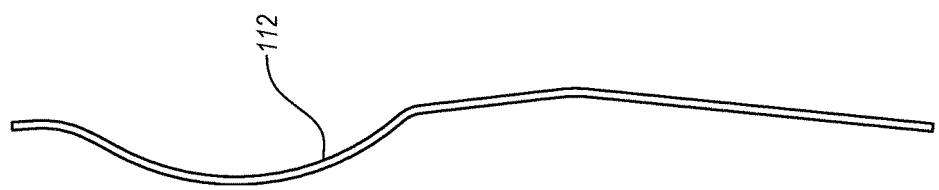
FIG. 6 is a side view of the wrist brace insert of a combination wrist and thumb brace.

The wrist brace portion 101 incorporates a rigid wrist brace insert 112 (see also FIG. 6) that extends along a length of the wrist brace portion 101 and is configured to stabilize a user's wrist when the brace 100 is in use. In various embodiments this rigid wrist brace insert 112 may be located within an interior sleeve of the wrist brace portion 101. The rigid wrist brace insert 112 may be constructed of metal, plastic, or any other rigid material. In various embodiments, other sleeves may be incorporated into the wrist brace portion, and be combined with other rigid inserts in order to give the wrist brace portion 101 form, shape, and/or additional support. The wrist brace portion 101 may also have one or more sleeves 113*a*, 113*b* on a side to receive components, e.g., the thumb brace portion 110, as described in further detail below.

The thumb brace portion 110 is comprised of a thumb portion 102 which is located adjacent to a distal end of the thumb brace portion 110, and a rigid thumb member 111 which stabilizes the thumb portion, user's thumb, and in the illustrated embodiment, wrist, when the thumb brace portion 110 is attached to the brace 100. The thumb portion 102 generally forms a tunnel to retain a user's thumb, and may have one or more support straps 207 which may be wrapped perpendicularly to and around the thumb portion 110 in order to secure and support a user's thumb. In various embodiments, the rigid thumb member 111 attaches to the brace 100 when the rigid thumb member 111 slides into a right sleeve 113a contained on the wrist brace portion 101. In various embodiments, the thumb brace portion 110 may also be capable of attachment to the wrist brace portion through a fastener 502, e.g., a Velcro strap, etc. Configured as described, the brace 100 supports a user's right hand and thumb in a right handed configuration A.

Figure 4:
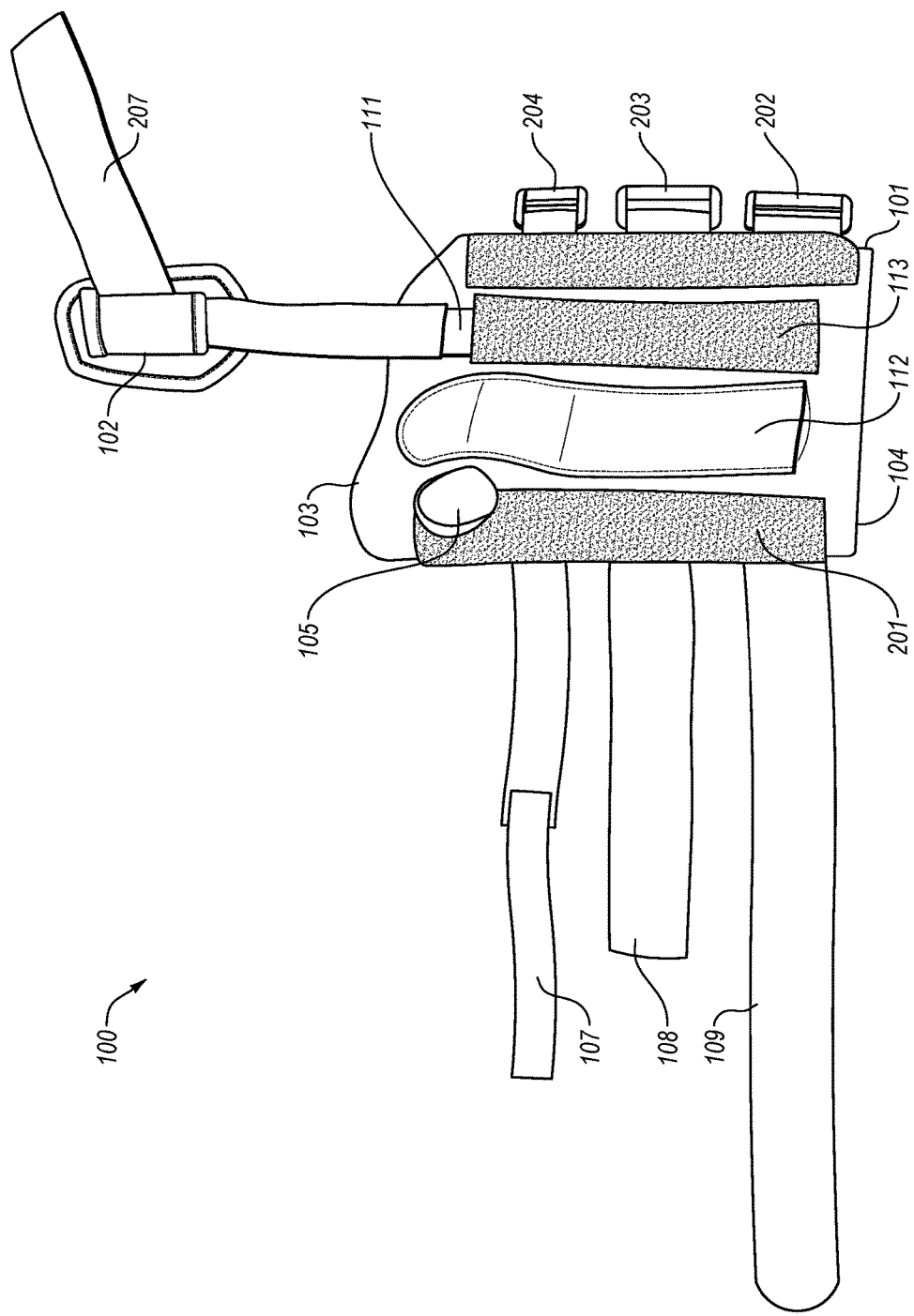
FIG. 4 is an alternate front view of a combination wrist and thumb brace.
Figure 5:
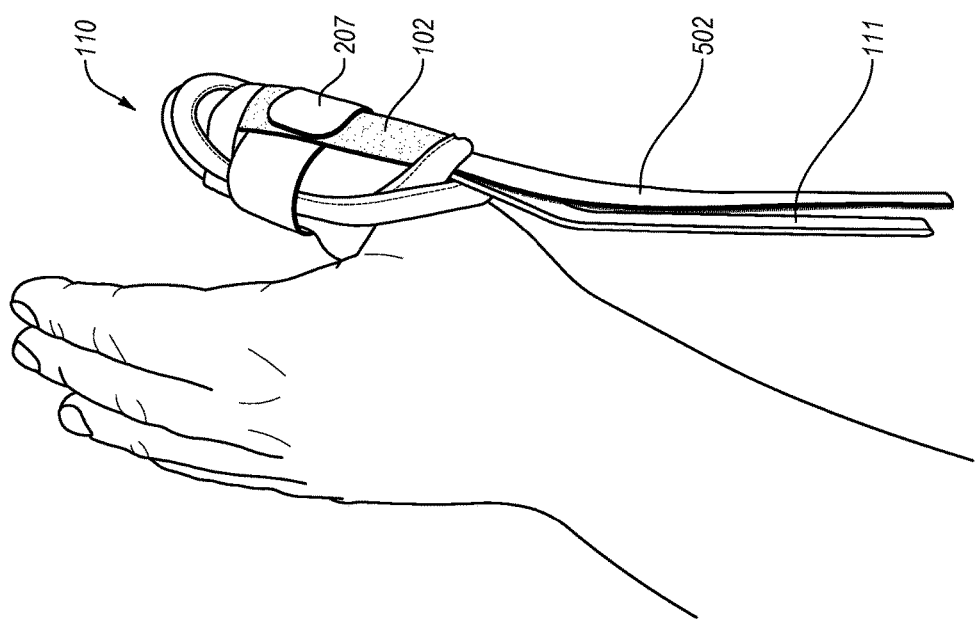
FIG. 5 is a perspective view of the thumb brace portion of a combination wrist and thumb brace.

Thumb brace portion 110 is fully detachable from the wrist brace portion 101 (see FIGS. 3, 4, 5). Referring now to FIG. 3, the brace 100 is capable of left-hand stabilization by removing the thumb brace portion 110 from the right sleeve 113a (see FIG. 4) and placing it into a left sleeve 201 contained on the left side of the wrist brace portion 101. Accordingly, the brace 100 is capable of operation in a left-handed configuration B. Alternatively, the thumb brace portion 110 may be removed altogether and not used with the wrist brace portion 101 in order to achieve a wrist-only support without thumb stabilization. So constructed, the brace 100 may be alternatively utilized as: (1) a right-hand combination wrist and thumb brace; (2) a left-hand combination wrist and thumb brace; (3) a right-hand wrist brace; and/or (4) a left hand wrist brace. Thus configured, the brace effectively comprises a "four in one" brace unit, thereby eliminating the need of obtaining, inventorying, carrying, and/or applying a variety of different braces and SKUs to different situations.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

I claim:

1. A wrist and thumb brace comprised of:
  a wrist brace portion for stabilizing a user's wrist, the wrist brace portion having a first aperture adapted for a user's right thumb when the wrist and thumb brace is on a user's right hand, and a second aperture adapted for a user's left thumb when the wrist and thumb brace is on a user's left hand, the first and second apertures configured to facilitate ambidextrous use of the wrist and thumb brace; and
  a thumb brace portion for stabilizing a user's thumb, the thumb brace portion removably attachable to the wrist brace portion at a first location adjacent to the first aperture when the wrist and thumb brace is on a user's right hand, the thumb brace portion removably attachable to the wrist brace portion at a second location adjacent to the second aperture when the wrist and thumb brace is on a user's left hand;
  the wrist brace portion having one or more sleeves each of which is adapted for receiving a rigid thumb member adapted to slide into the one or more sleeves for releasably attaching the thumb brace portion to the wrist brace portion, the rigid thumb member further being a plate.

2. The wrist and thumb brace of claim 1, the thumb brace portion further comprised of a thumb portion located adjacent to a distal end of the thumb brace portion, the thumb portion having one or more straps for securing a user's thumb to the rigid thumb member.

3. The wrist and thumb brace of claim 2, the thumb brace portion further having a fastener for securing and retaining the thumb brace portion to the wrist brace portion.

4. A wrist and thumb brace comprised of:
  a wrist brace portion for stabilizing a user's wrist, the wrist brace portion having a first aperture adapted for a user's right thumb when the wrist and thumb brace is on a user's right hand, and a second aperture adapted for a user's left thumb when the wrist and thumb brace is on a user's left hand, the first and second apertures configured to facilitate ambidextrous use of the wrist and thumb brace, the wrist brace portion further operable to secure the wrist and thumb brace onto a user's wrist with a plurality of support straps capable of orientation perpendicular to the wrist brace portion; and
  a thumb brace portion for stabilizing a user's thumb, the thumb brace portion removably attachable to the wrist brace portion at a first location adjacent to the first aperture when the wrist and thumb brace is on a user's right hand, the thumb brace portion removably attachable to the wrist brace portion at a second location adjacent to the second aperture when the wrist and thumb brace is on a user's left hand, the thumb brace portion further comprised of a thumb portion located adjacent to a distal end of the thumb brace portion, the thumb portion having one or more straps for securing a user's thumb to the rigid thumb member, the thumb brace portion further having a fastener for securing and retaining the thumb brace portion to the wrist brace portion;
  the wrist brace portion having one or more sleeves each of which is adapted for receiving a rigid thumb member adapted to slide into the one or more sleeves for releasably attaching the thumb brace portion to the wrist brace portion, the rigid thumb member further being a plate.

5. The wrist and thumb brace of claim 4, wherein the plurality of support straps are capable of orientation perpendicular to the wrist brace portion and adapted to secure the wrist and thumb brace onto a user's wrist through a cinch and loop system.

6. The wrist and thumb brace of claim 4, wherein the wrist and thumb brace is capable of use solely as a wrist brace by removing the thumb brace portion.

7. The wrist and thumb brace of claim 4 wherein rigid thumb member is adapted to be placed adjacent to an outer portion of a user's thumb when the wrist and thumb brace is in use.

8. A wrist and thumb brace comprised of:
  a wrist brace portion for stabilizing a user's wrist, the wrist brace portion having a first aperture adapted for a user's right thumb when the wrist and thumb brace is on a user's right hand, and a second aperture adapted for a user's left thumb when the wrist and thumb brace is on a user's left hand, the first and second apertures configured to facilitate ambidextrous use of the wrist and thumb brace, the wrist brace portion further operable to secure the wrist and thumb brace onto a user's wrist with a plurality of support straps capable of orientation perpendicular to the wrist brace portion, the plurality of support straps capable of orientation perpendicular to the wrist brace portion and adapted to secure the wrist and thumb brace onto a user's wrist through a cinch and loop system, the wrist brace portion further having one or more sleeves each of which is adapted for receiving a rigid thumb member adapted to slide into the one or more sleeves for releasably attaching a thumb brace portion to the wrist brace portion, the rigid thumb member further being a plate adapted to be placed adjacent to an outer portion of a user's thumb when the wrist and thumb brace is in use; and the thumb brace portion being for stabilizing a user's thumb, the thumb brace portion removably attachable to the wrist brace portion at a first location adjacent to the first aperture when the wrist and thumb brace is on a user's right hand, the thumb brace portion removably attachable to the wrist brace portion at a second location adjacent to the second aperture when the wrist and thumb brace is on a user's left hand, the thumb brace portion further comprised of a thumb portion located adjacent to a distal end of the thumb brace portion, the thumb portion having one or more straps for securing a user's thumb to the rigid thumb member, the thumb brace portion further having a fastener for securing and retaining the thumb brace portion to the wrist brace portion;

the wrist and thumb brace capable of use solely as a wrist brace by removing the thumb brace portion.

\* \* \* \* \*